United States Patent [19]

Moore

[11] Plant 4,231

[45] Mar. 28, 1978

[54] ROSE PLANT

[76] Inventor: Ralph S. Moore, 2519 E. Noble Ave., Visalia, Calif. 93277

[21] Appl. No.: 805,609

[22] Filed: Jun. 10, 1977

[51] Int. Cl.[2] ..... A01H 5/00
[52] U.S. Cl. ..... Plt./3
[58] Field of Search ..... Plt/3/

*Primary Examiner*—Robert E. Bagwill

[57] ABSTRACT

This invention relates to a new and distinct variety of miniature rose plant characterized by its buds and flowers of rich deep yellow color, borne in abundance throughout the growing season, and further characterized by the bushy upright plant, well branched from the base, which is easy to propagate from cuttings.

1 Drawing Figure

The present invention relates to a new and distinct variety of hardy, dwarf, bush type rose plant of the miniature class; the variety being primarily characterized — as to novelty — by clear yellow buds and flowers which in general color effect are similar to Golden Angel (miniature — U.S. Plant Pat. No. 4028).

The variety is further characterized by:

An abundance of bloom, with flowers borne singly or several to the stem in loose clusters.

Sweet rose fragrance.

A plant which is vigorous, of rounded upright shape and with small semi-glossy to matt foliage with pointed leaflets; the buds and flowers being similar in form and size to Bit O'Sunshine (miniature — U.S.Plant Pat. No. 1,631, expired) and the flowers being more fully double.

The plant, which has a normal height of 14–16 inches, can easily be maintained at lesser height by occasional trimming.

A plant which grows and blooms satisfactorily both in greenhouse and outdoors; is good for growing in pots and provides excellent garden decoration as well as cut flowers.

The present variety of miniature rose was originated by me at my nursery located at Visalia, Calif., under conditions of careful control and observation as a cross between Little Darling (Floribunda — U.S. Plant Pat. No. 1,581, expired) as the seed parent and Yellow Magic (Miniature — not patented), as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of minature rose plant, the following is a detailed description thereof in outline; all major color plate identifications being by reference to the British Colour Council Horticultural Colour Chart, except where common terms of color definition are employed.

Type: Hardy, dwarf; busy rounded; upright; seedling; greenhouse; outdoors; cut flowers; garden decoration; potted plant.

Class: Miniature. Variety name: Rise'n Shine.

Flowers: Continuity; continuous — repeat bloom all season. Fragrance; sweet tea rose.

Flowers borne: Singly and several together (three to five sometimes more) on tips of main shoots and on shorter lateral shoots.

Quantity of bloom: Abundant both outside and in greenhouse.

Bud: Peduncle — medium length; slender but sturdy; erect; medium green, sometimes tinted bronze (outdoors); Hairs — numerous, very short, very soft hairs. Before calyx breaks; size — small. Form long; pointed with several foliaceous appendages and few or no hairs on surface of bud; with foliaceous parts extending beyond the tip of the bud equal to one-half or more of its length. Color — medium green, occasionally tinted with bronze (outdoors). As calyx breaks, color — clear yellow/ near Saffron Yellow 7/2. Opening: opens well in all weather; color near Indian Yellow 6/2; size — small.

Bloom: Size when fully open — small, averaging about 35 mm. Petalage — double — 25 to 40 petals, arranged regularly plus sometimes several small petaloids. Form — flat to slightly rounded at first, becoming more open in the center, with petals rolled loosely outward, and later at maturity open with petals folded at tips to give a pointed effect resembling a Hybrid Cactus type dahlia in general form. Fully open flowers usually show stamens.

Petals: Fairly thick; satiny on inside and on outside surface. Shape — outside petals, broad lanceolate with small acute tip; intermediate — broad lanceolate with acute tip; inside — lanceolate with acute tip.

Color: Newly opened flower from a plant growing in plastic greenhouse (April 1977), Visalia, Calif.

*Outside petal.*—Outside surface — near Indian Yellow 6/2 becoming darker yellow on basal half of petal; inside surface — near Indian Yellow 6/2 shading darker on basal one half of petal to near Buttercup Yellow 5/1 at base.

*Intermediate petal.*—Outside surface — similar to outside petal. Inside surface — similar to outside petal.

*Inner petal.*—Outside surface — same as intermediate petal; Inside surface — same as itermediate petal. General color effect newly opened flowers — clear yellow. Three days open — color similar to newly opened flowers but lighter color. Behavior — due to clutural factors such as soil fertility, light intensity, day length, etc., the intensity of the yellow color may vary. Spent petals drop off. Flower longevity (October 1976) — plant in pot 5–7 days or longer. Cut flowers at living room temperature 4–5 days or longer.

Reproductive organs:

*Stamens.*—Abundant, arranged regularly about pistil.

*Filaments.*—Varying length, yellow.

*Anthers.*—Well formed; yellow.

*Pollen.*—Moderate amount.

*Pistils.*—Average number.

*Styles.*—Fairly even; medium length; bunched; color — reddish.

*Stigma.*—Yellow.

*Ovaries.*—All enclosed in calyx.

*Hips.*—Several.

*Sepals.*—Permanent; spear shaped; recurved.

*Seed.*—Few to several.

Foliage:

*Leaves.*—Compound of five (sometimes three or seven). Leaflets: abundant; quite small; leathery; semi-glossy to matt.

Leaflets — shape: broad, lanceolate; apex acute; base rounded or rounded acute. Margin serrate.

*Color.*—Medium green; new growth — normal (medium) green, sometimes reddish (outdoors).

*Rachis.*—Medium strength; upper side may have a few tiy short hairs or prickles, grooved; underside sparsely thorny with few or no tiny prickles.

*Stipules.*—Medium long; narrow to medium width, with numerous hairs along margins; medium length narrow points which turn out usually at about 45°.

Growth:

*Habit.*—Dwarf; bushy; upright; much branched.

*Growth.*—Free vigorous; internodes fairly short.

*Canes.*—Medium; slender; sturdy.

*Main stems.*—Color: medium green.

*Thorns.*—Average; fairly long; slender; hooked slightly downward; color; brown. Prickles — none. Hairs — none.

*Branches.*—Color: light to medium green. Thorns: average; fairly long; slender; nearly straight. Medium to short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit substantially as illustrated and described, characterized by buds and flowers which are generally of a clear yellow color, the center of opening buds and flowers at times tending to be deeper yellow (or gold yellow); with buds and flowers being similar in size and shape to Bit O'Sunshine (U.S. Plant Pat. No. 1,631, expired) but having more petals; and further characterized by a plant similar to Yellow Magic (miniature, not patented) which is vigorous and compact, the shoots and branches having fairly short internodes, said plant being easy to propagate from cuttings; and having an abundance of semi-glossy to matt foliage, with flowers borne singly or several to the stem in loose clusters.

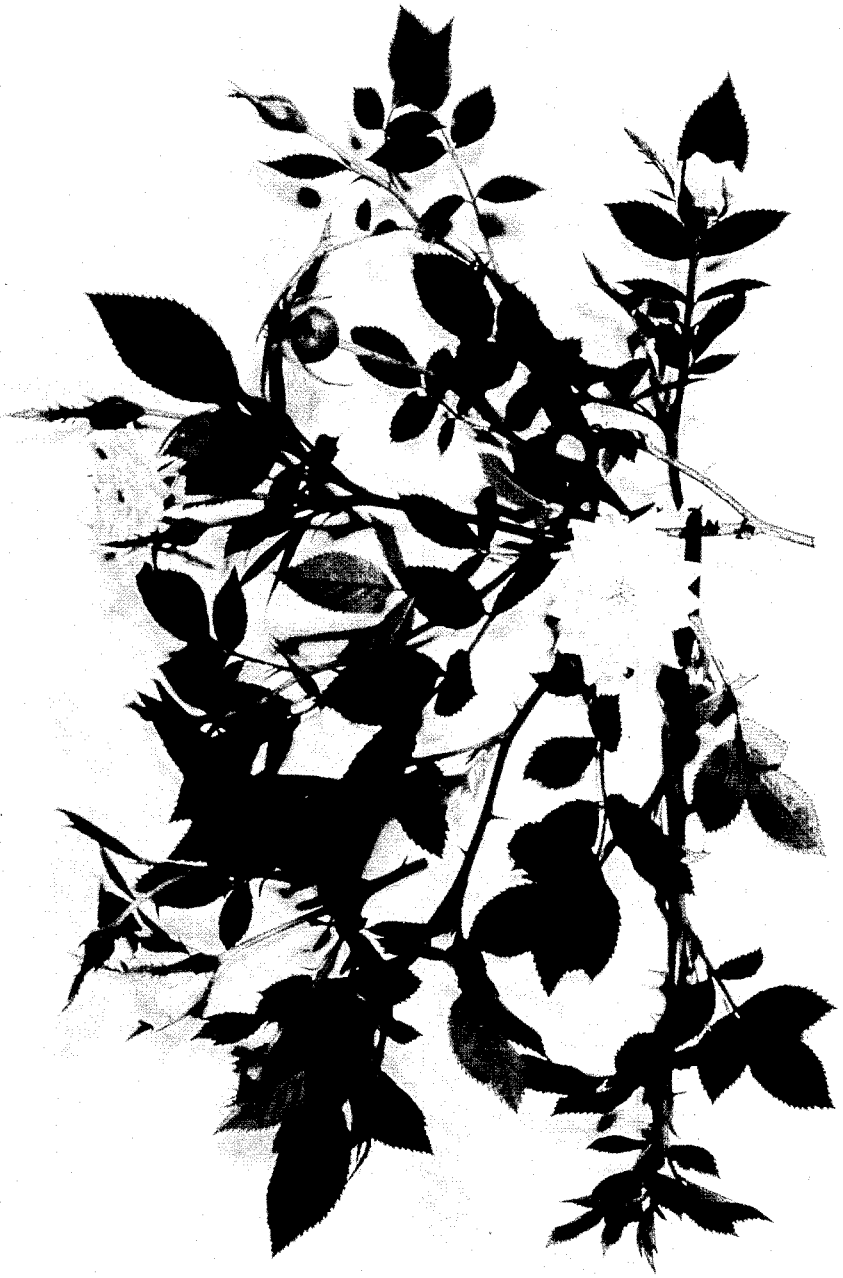

* * * * *